(12) United States Patent  
Opolski

(10) Patent No.: US 8,372,113 B2  
(45) Date of Patent: Feb. 12, 2013

(54) CURVED ARM INTRACARDIAC OCCLUDER

(75) Inventor: Steven W. Opolski, Carlisle, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 910 days.

(21) Appl. No.: 11/377,038

(22) Filed: Mar. 16, 2006

(65) Prior Publication Data  
US 2006/0217761 A1 Sep. 28, 2006

Related U.S. Application Data

(60) Provisional application No. 60/664,988, filed on Mar. 24, 2005.

(51) Int. Cl.  
A61B 17/08 (2006.01)

(52) U.S. Cl. ........................ 606/213; 606/151

(58) Field of Classification Search ................ 606/213, 606/151, 139, 1, 153, 157, 200, 215  
See application file for complete search history.

(56) References Cited

U.S. PATENT DOCUMENTS

| | | |
|---|---|---|
| 3,874,388 A | 4/1975 | King et al. |
| 4,007,743 A | 2/1977 | Blake |
| 4,696,300 A | 9/1987 | Anderson |
| 4,710,192 A | 12/1987 | Liotta et al. |
| 4,836,204 A | 6/1989 | Landymore et al. |
| 4,917,089 A | 4/1990 | Sideris |
| 5,108,420 A | 4/1992 | Marks |
| 5,171,259 A | 12/1992 | Inoue |
| 5,284,488 A | 2/1994 | Sideris |
| 5,312,341 A | 5/1994 | Turi |
| 5,334,217 A | 8/1994 | Das |
| 5,425,744 A | 6/1995 | Fagan et al. |
| 5,433,727 A | 7/1995 | Sideris |
| 5,451,235 A | 9/1995 | Lock et al. |
| 5,507,811 A | 4/1996 | Koike et al. |
| 5,578,045 A | 11/1996 | Das |
| 5,597,378 A | 1/1997 | Jervis |
| 5,634,936 A | 6/1997 | Linden et al. |
| 5,702,421 A | 12/1997 | Schneidt |
| 5,709,707 A | 1/1998 | Lock et al. |
| 5,725,552 A | 3/1998 | Kotula et al. |
| 5,733,294 A | 3/1998 | Forber et al. |
| 5,741,297 A | 4/1998 | Simon |
| 5,797,960 A | 8/1998 | Stevens et al. |
| 5,823,956 A | 10/1998 | Roth et al. |
| 5,829,447 A | 11/1998 | Stevens et al. |

(Continued)

FOREIGN PATENT DOCUMENTS

| | | |
|---|---|---|
| EP | 1 013 227 A2 | 6/2000 |
| EP | 1 046 375 A1 | 10/2000 |

(Continued)

OTHER PUBLICATIONS

Cook Incorporated product brochure for "Bird's Nest® Vena Cava Filter," (2000).

(Continued)

Primary Examiner — Corrine M McDermott  
Assistant Examiner — Mark Mashack  
(74) Attorney, Agent, or Firm — DLA Piper LLP (US)

(57) ABSTRACT

Disclosed herein are devices and methods for occluding intracardiac defects, for example, a patent foramen ovale (PFO). The devices according to the invention have various features that enhance the flexibility of the device and improve the device's ability to conform to the location of the intracardiac defect. In particular, intracardiac occluders with curved arms are disclosed.

12 Claims, 9 Drawing Sheets

U.S. PATENT DOCUMENTS

| | | | |
|---|---|---|---|
| 5,853,422 A | 12/1998 | Huebsch et al. | |
| 5,855,614 A * | 1/1999 | Stevens et al. | 128/898 |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A * | 4/1999 | Jacob et al. | 606/151 |
| 5,904,703 A | 5/1999 | Gilson | |
| 5,919,200 A | 7/1999 | Stambaugh et al. | |
| 5,924,424 A | 7/1999 | Stevens et al. | |
| 5,944,738 A | 8/1999 | Amplatz et al. | |
| 5,976,174 A * | 11/1999 | Ruiz | 606/213 |
| 5,997,556 A | 12/1999 | Tanner | |
| 6,010,517 A | 1/2000 | Baccaro | |
| 6,024,756 A | 2/2000 | Huebsch et al. | |
| 6,077,291 A | 6/2000 | Das | |
| 6,079,414 A | 6/2000 | Roth | |
| 6,080,182 A | 6/2000 | Shaw et al. | |
| 6,106,532 A | 8/2000 | Koike et al. | |
| 6,113,609 A | 9/2000 | Adams | |
| 6,117,159 A | 9/2000 | Huebsch et al. | |
| 6,132,438 A | 10/2000 | Fleischman et al. | |
| 6,152,144 A | 11/2000 | Lesh et al. | |
| 6,165,183 A | 12/2000 | Kuehn et al. | |
| 6,171,329 B1 | 1/2001 | Shaw et al. | |
| 6,174,322 B1 | 1/2001 | Schneidt | |
| 6,206,907 B1 | 3/2001 | Marino et al. | |
| 6,214,029 B1 | 4/2001 | Thill et al. | |
| 6,221,092 B1 | 4/2001 | Koike et al. | |
| 6,231,561 B1 | 5/2001 | Frazier et al. | |
| 6,270,515 B1 | 8/2001 | Linden et al. | |
| 6,290,674 B1 | 9/2001 | Roue et al. | |
| 6,312,446 B1 | 11/2001 | Huebsch et al. | |
| 6,328,727 B1 | 12/2001 | Frazier et al. | |
| 6,348,041 B1 | 2/2002 | Klint | |
| 6,352,531 B1 | 3/2002 | O'Connor et al. | |
| 6,352,552 B1 | 3/2002 | Levinson et al. | |
| 6,355,052 B1 | 3/2002 | Neuss et al. | |
| 6,375,671 B1 | 4/2002 | Kobayashi et al. | |
| 6,379,368 B1 | 4/2002 | Corcoran et al. | |
| 6,383,146 B1 | 5/2002 | Klint | |
| 6,387,060 B1 | 5/2002 | Jalisi | |
| 6,387,104 B1 * | 5/2002 | Pugsley et al. | 606/139 |
| 6,419,669 B1 | 7/2002 | Frazier et al. | |
| 6,436,088 B2 | 8/2002 | Frazier et al. | |
| 6,440,152 B1 | 8/2002 | Gainor et al. | |
| 6,482,210 B1 | 11/2002 | Skiba et al. | |
| 6,488,706 B1 | 12/2002 | Solymar | |
| 6,544,272 B1 * | 4/2003 | Jakob et al. | 606/151 |
| 6,551,303 B1 | 4/2003 | Van Tassel et al. | |
| 6,551,344 B2 | 4/2003 | Thill | |
| 6,596,013 B2 | 7/2003 | Yang et al. | |
| 6,616,685 B2 * | 9/2003 | Rousseau | 606/213 |
| 6,623,508 B2 | 9/2003 | Shaw et al. | |
| 6,623,518 B2 | 9/2003 | Thompson et al. | |
| 6,656,206 B2 * | 12/2003 | Corcoran et al. | 606/213 |
| 6,666,873 B1 * | 12/2003 | Cassell | 606/153 |
| 6,712,836 B1 | 3/2004 | Berg et al. | |
| 2001/0034537 A1 | 10/2001 | Shaw et al. | |
| 2001/0037129 A1 | 11/2001 | Thill | |
| 2001/0041914 A1 | 11/2001 | Frazier et al. | |
| 2001/0041915 A1 | 11/2001 | Roue et al. | |
| 2002/0010481 A1 | 1/2002 | Jayaraman | |
| 2002/0029048 A1 | 3/2002 | Miller | |
| 2002/0035374 A1 | 3/2002 | Borillo et al. | |
| 2002/0077555 A1 | 6/2002 | Schwartz | |
| 2002/0111636 A1 * | 8/2002 | Fleischman et al. | 606/139 |
| 2002/0111647 A1 | 8/2002 | Khairkhahan et al. | |
| 2002/0128680 A1 | 9/2002 | Pavlovic | |
| 2002/0183786 A1 | 12/2002 | Girton | |
| 2002/0183787 A1 | 12/2002 | Wahr et al. | |
| 2003/0028213 A1 | 2/2003 | Thill et al. | |
| 2003/0045893 A1 | 3/2003 | Ginn | |
| 2003/0045901 A1 | 3/2003 | Opolski | |
| 2003/0050665 A1 | 3/2003 | Ginn | |
| 2003/0065379 A1 | 4/2003 | Babbs et al. | |
| 2003/0073979 A1 | 4/2003 | Naimark et al. | |
| 2003/0139819 A1 | 7/2003 | Beer et al. | |
| 2003/0144694 A1 | 7/2003 | Chanduszko et al. | |
| 2003/0171739 A1 * | 9/2003 | Murphy et al. | 606/1 |
| 2003/0191495 A1 | 10/2003 | Ryan et al. | |
| 2003/0191526 A1 | 10/2003 | Van Tassel et al. | |
| 2003/0195530 A1 | 10/2003 | Thill | |
| 2003/0195531 A1 | 10/2003 | Gardiner et al. | |
| 2003/0204203 A1 | 10/2003 | Khairkhahan et al. | |
| 2004/0044361 A1 | 3/2004 | Frazier et al. | |
| 2004/0143277 A1 | 7/2004 | Marino et al. | |
| 2004/0143291 A1 * | 7/2004 | Corcoran et al. | 606/213 |
| 2004/0143293 A1 | 7/2004 | Marino et al. | |
| 2004/0143294 A1 | 7/2004 | Corcoran et al. | |
| 2004/0176799 A1 * | 9/2004 | Chanduszko et al. | 606/213 |
| 2004/0210301 A1 | 10/2004 | Obermiller | |
| 2004/0220596 A1 | 11/2004 | Frazier et al. | |
| 2004/0267191 A1 | 12/2004 | Gifford, III et al. | |
| 2004/0267306 A1 * | 12/2004 | Blaeser et al. | 606/213 |
| 2005/0065547 A1 * | 3/2005 | Marino et al. | 606/213 |
| 2005/0070957 A1 * | 3/2005 | Das | 606/213 |
| 2005/0125032 A1 | 6/2005 | Whisenant et al. | |
| 2005/0131460 A1 | 6/2005 | Gifford, III et al. | |
| 2005/0192627 A1 * | 9/2005 | Whisenant et al. | 606/213 |
| 2005/0273119 A1 * | 12/2005 | Widomski et al. | 606/151 |
| 2006/0155327 A1 * | 7/2006 | Briganti et al. | 606/213 |
| 2010/0234880 A1 * | 9/2010 | Abbott et al. | 606/213 |

FOREIGN PATENT DOCUMENTS

| | | |
|---|---|---|
| EP | 0 724 406 B1 | 12/2001 |
| EP | 1 222 897 A2 | 7/2002 |
| GB | 2 407 985 A | 5/2005 |
| WO | WO 95/10983 | 4/1995 |
| WO | WO 98/38920 | 9/1998 |
| WO | WO 98/39053 | 9/1998 |
| WO | WO 98/39063 | 9/1998 |
| WO | WO 99/05977 | 2/1999 |
| WO | WO 99/25254 | 5/1999 |
| WO | WO 99/30640 | 6/1999 |
| WO | WO 00/27292 | 5/2000 |
| WO | WO 01/08600 | 2/2001 |
| WO | WO 01/30266 | 5/2001 |
| WO | WO 01/30267 | 5/2001 |
| WO | WO 01/30268 | 5/2001 |
| WO | WO 01/49185 | 7/2001 |
| WO | WO 01/93783 | 12/2001 |
| WO | WO 02/24106 | 3/2002 |
| WO | WO 03/022159 | 3/2003 |
| WO | WO 03/059152 | 7/2003 |
| WO | WO 03/061481 | 7/2003 |
| WO | WO 03/073944 | 9/2003 |
| WO | WO 03/103476 | * 12/2003 |
| WO | WO 2004/028348 | 4/2004 |

OTHER PUBLICATIONS

Hanson, (1981), "Metals that Remember," *Science*, (81):44-47.

Kramer, (2003), "PFO and Stroke: The Hidden Connection," *Endovascular Today*, available at http://www.evtoday.com/03_archive/0903/101.html, accessed on Apr. 21, 2004.

Latson, (1993), "Transcatheter Closure of Atrial Septal Defects," Chapter 17 in *Transcatheter Therapy in Pediatric Cardiology*, pp. 335-348, Wiley and Sons, Inc.

Simon et al., (1977), "A Vena Cava Filter Using Thermal Shape Memory Alloy," *Radiology*, 125(1):89-94.

Simon et al., (1980), "Transvenous Devices for the Management of Pulmonary Embolism," *Cardiovascular and Internventional Radiology*, 3:308-318.

Stöckel, (2000), "Nitinol Medical Devices and Implants," *Proceedings of the International Conference on Shape Memory and Superelastic Technologies*, pp. 532-541.

Szili-Torok et al., (2001), "Transseptal Left Heart Catherisation Guided by Intracardiac Echocardiography," *Heart*, (86):e11.

* cited by examiner

CURVED ARM INTRACARDIAC OCCLUDER

RELATED APPLICATIONS

This application claims priority to and benefit of U.S. Provisional application 60/664,988, filed on Mar. 24, 2005, the entirety of which is incorporated by reference herein.

TECHNICAL FIELD OF THE INVENTION

The invention generally relates to devices and related methods for treating intracardiac defects. More particularly, the invention provides an intracardiac occluder for the percutaneous closure of intracardiac defects.

BACKGROUND OF THE INVENTION

The human heart is divided into four compartments or chambers. The left and right atria are located in the upper portion of the heart and the left and right ventricles are located in the lower portion of the heart. The left and right atria are separated from each other by a muscular wall, the interatrial septum, while the ventricles are separated by the interventricular septum.

Either congenitally or by acquisition, abnormal openings, holes, or shunts can occur between the chambers of the heart or between the great vessels, causing blood to flow along an anomalous pathway therethrough. Such deformities are usually congenital and originate during fetal life when the heart forms from a folded tube into a four chambered, two unit system. The deformities result from the incomplete formation of the septum, or muscular wall, between the chambers of the heart and can cause significant problems. Ultimately, the deformities add strain on the heart, which may result in heart failure if they are not corrected.

One such deformity or defect, a patent foramen ovale (PFO), is a persistent, one-way, usually flap-like opening in the wall between the right atrium and left atrium of the heart. Since left atrial pressure is normally higher than right atrial pressure, the flap typically stays closed. Under certain conditions, however, right atrial pressure exceeds left atrial pressure, creating the possibility for right to left shunting that can allow blood clots to enter the systemic circulation. This is particularly worrisome to patients who are prone to forming venous thrombi, such as those with deep vein thrombosis or clotting abnormalities.

Nonsurgical (i.e., percutaneous) closure of a PFO, as well as similar intracardiac defects such as an atrial septal defect, a ventricular septal defect, and closure of the left atrial appendage, is possible using a variety of mechanical closure devices. These percutaneously, transvascularly introduced devices, which avoid the potential side effects often associated with standard anticoagulation therapy of a patient having one of these defects, typically consist of a metallic structural framework that is combined with a synthetic or biological tissue scaffold material applied to the structural framework.

The structural framework of the prior art intracardiac occluders are often stiff and rigid, lacking the flexibility necessary to conform with irregularly shaped intracardiac defects. This results in trauma to surrounding tissues, chronic inflammation, residual leaks, and even breakage of the occluder, impairing closure of the defect to which the intracardiac occluder is applied.

SUMMARY OF THE INVENTION

The present invention provides a device for occluding intracardiac defects. The device includes a proximal occlusion shell comprising a flexible and resilient support structure and a scaffold material. The proximal occlusion shell is connected to a distal occlusion shell by a central body portion. The support structure comprises a variety of modifications that enhance the flexibility of the device.

In one aspect of the invention, the intracardiac occluder comprises a central body portion, a proximal occlusion shell and a distal occlusion shell. The proximal occlusion shell comprises a plurality of arms, at least one of the arms comprising a curve extending from a hub end of the arm to a free end of the arm in a constantly changing plane around a central axis. The central body portion is secured between the proximal occlusion shell and the distal occlusion shell for positioning the device in a defect. In another embodiment, the proximal occlusion shell comprises a second arm comprising a curve extending from a hub end to a free end in a constantly changing plane around a central axis. The second arm may curve in a direction opposite the direction of the at least one arm comprising a curve, or it may curve in the same direction. The second arm comprising a curve and the at least one arm comprising a curve may also be adjacent to one another. In a further embodiment, the proximal occlusion shell further comprises at least one arm wherein the arm curves such that the free end of the at least one arm is in the same plane as the hub end of the arm and all other points on that arm.

In a further embodiment, an arm of a proximal occlusion shell is made of a material selected from the group consisting of nitinol, MP35N, polymers, bioresorbable polymers, and a metal. In yet another embodiment at least one arm of the proximal occlusion shell comprises a plurality of wires, while in a further embodiment, the cross-section of at least one of the wires is selected from the group consisting of a circle, a triangle, a square, a rectangle, and an oval. In another embodiment, the arms are joint-free.

In another aspect of the invention, an intracardiac occluder comprises a central body portion, a proximal occlusion shell and a distal occlusion shell. The proximal occlusion shell comprises a plurality of arms, each arm extending from a hub end to a free end, wherein at least one of the plurality of arms comprises a curve extending from the hub end to the free end and at least another of the plurality of arms is straight. The central body portion is secured between said proximal occlusion shell and said distal occlusion shell for positioning the device in a defect. In one embodiment, at least one arm of a proximal occlusion shell comprises a curve extending from a hub end to a free end in a constantly changing plane around a central axis, while in a further embodiment, the free end of the at least one arm comprising a curve is in the same plane as the hub end and all other points on the at least one arm comprising a curve. In yet another embodiment, the at least one arm of the proximal occlusion shell comprising a curve extending from the hub end to the free end is adjacent to the at least one arm that is straight. In yet another embodiment, the proximal occlusion shell comprises at least one arm that is straight which differs in length compared to another arm that is straight, while in yet another embodiment, the proximal occlusion shell comprises at least one arm comprising a curve which differs in length compared to another arm that comprises a curve. In a further embodiment, the plurality of arms of the proximal occlusion shell are joint-free.

In another aspect of the invention, an intracardiac occluder comprises a central body portion, a proximal occlusion shell, and a distal occlusion shell. The proximal occlusion shell comprises a first arm comprising a curve extending from the hub end to the free end and a second arm comprising a curve extending from the hub end to the free end, the second arm curving in a direction opposite to the curving direction of the first arm, and the central body portion is secured between the proximal occlusion shell and the distal occlusion shell for positioning the device in a defect. In another embodiment, the second arm of the proximal occlusion shell comprising a curve is adjacent to the first arm comprising a curve. In a further embodiment, at least one of the first arm or the second arm of the proximal occlusion shell comprises a curve extending from the hub end to the free end in a constantly changing plane around a central axis, while in another embodiment, at least one of the first arm or the second arm of the proximal occlusion shell curves such that the hub end is in the same plane as the free end and all other points on the arm. In yet another embodiment, the hub end and the free end of the first arm of the proximal occlusion shell is in a first plane and the hub end and the free end of the second arm are in a second plane. In yet another embodiment, the proximal occlusion shell further comprises at least one straight arm, while in another embodiment, the plurality of arms are joint-free.

The foregoing and other objects, aspects, features and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 4A depicts a side view of an exemplary support frame of an occlusion shell of an intracardiac occluder including helically curved arms, while

DETAILED DESCRIPTION OF THE INVENTION

The present invention is directed to intracardiac occluders, such as intracardiac occluders, for the repair of intracardiac defects in a patient, such as, for example, a patent foramen ovale (PFO), an atrial septal defect, and a ventricular septal defect, and for occlusion of a left atrial appendage. All of the following embodiments of the invention include one or more features to improve the conformability and fatigue resistance of an intracardiac occluder at an intracardiac anatomical site such as an intracardiac defect, for example, a PFO.

Figure 1:
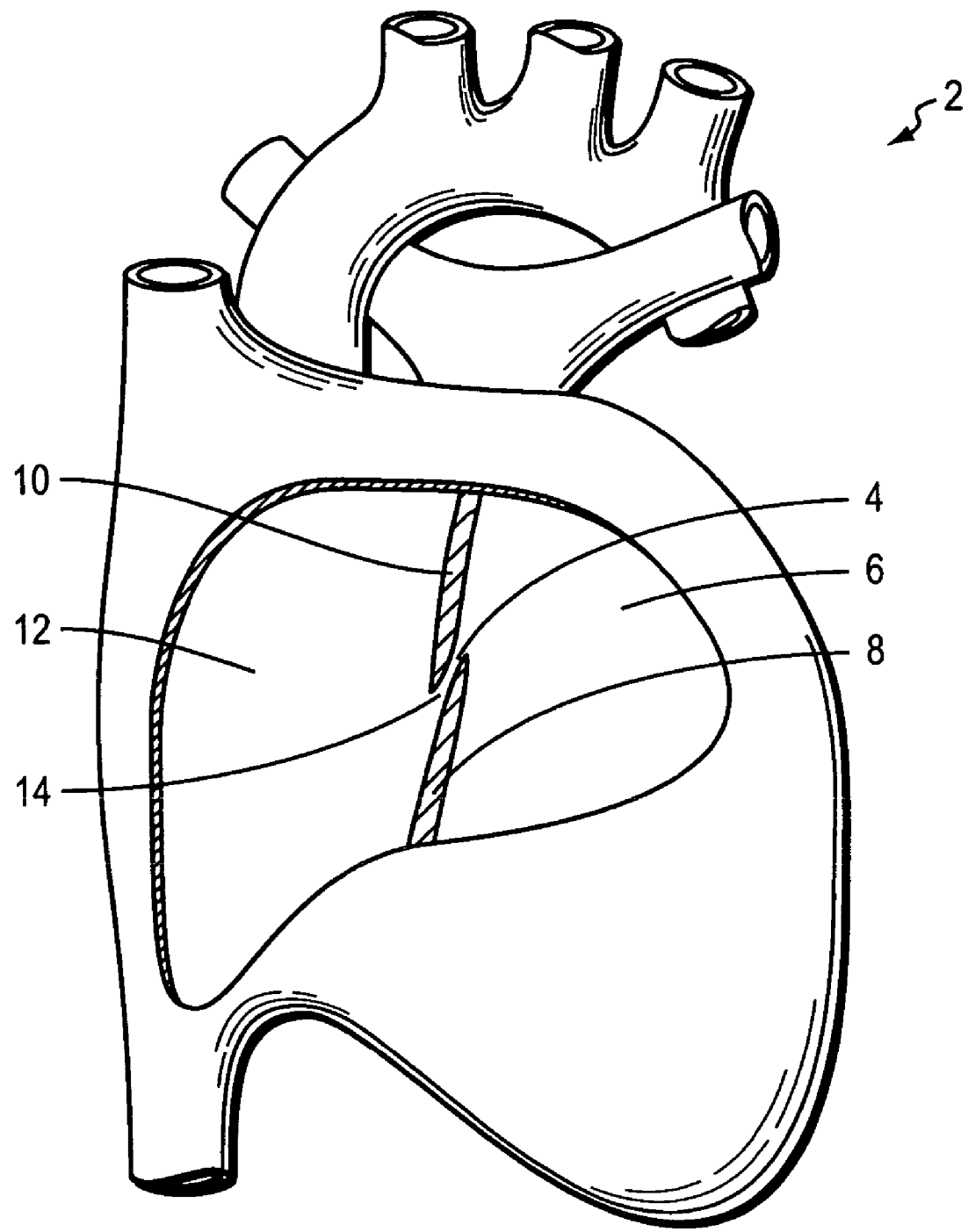
FIG. 1 depicts a cutaway view of the heart illustrating an exemplary intracardiac defect.

FIG. 1 depicts a cutaway view of a heart 2 illustrating an exemplary intracardiac defect 14. The heart 2 includes a septum 4 that divides the right atrium 12 from the left atrium 6. The septum 4 includes a septum primum 8, a septum secundum 10, and an exemplary intracardiac defect 14, which is to be corrected by the introduction of an intracardiac occluder of the present invention between the septum primum 8 and the septum secundum 10. Specifically, a PFO 14 is shown as an opening through the septum 4. The PFO 14 provides an undesirable fluid communication between the right atrium 12 and the left atrium 6. Under certain conditions, a large PFO 14 in the septum 4 would allow for the abnormal shunting of blood from the right atrium 12 to the left atrium 6. If the PFO 14 is not closed or obstructed in some manner, a patient is placed at high risk for an embolic stroke.

Figure 2A:
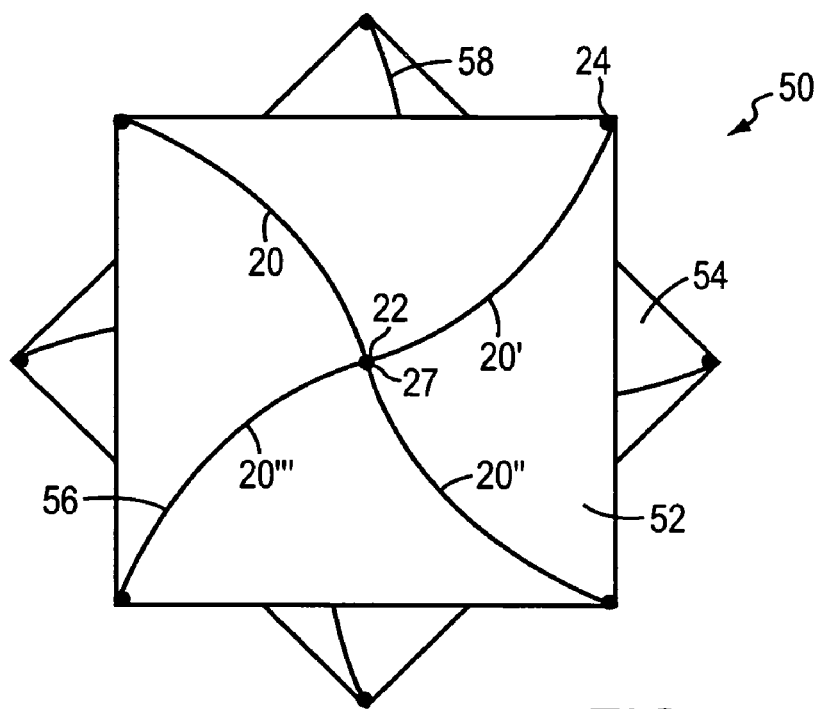
FIG. 2A depicts a top perspective view of an intracardiac occluder with curved arms according to an illustrative embodiment of the invention.
Figure 2B:
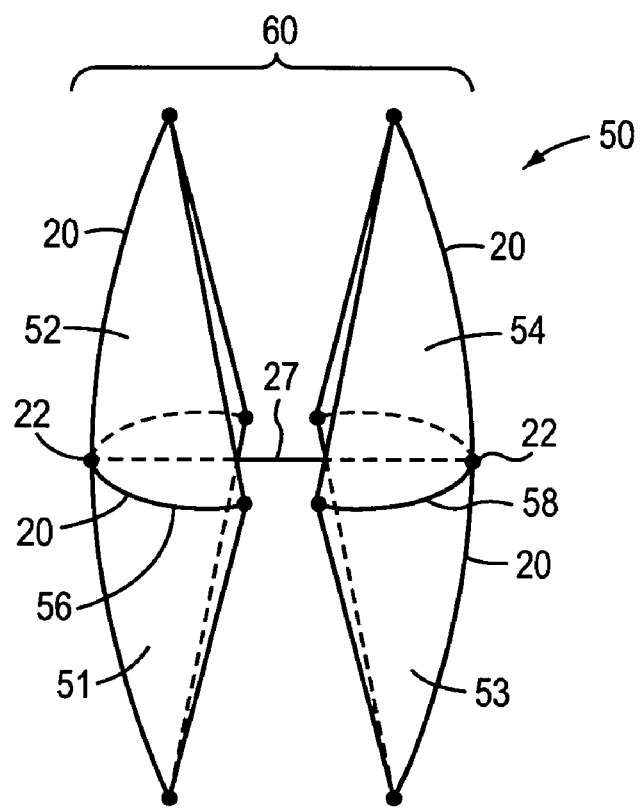
FIG. 2B depicts a side view of the intracardiac occluder illustrated in FIG. 2A.

FIG. 2A depicts a top perspective view of an intracardiac occluder with curved arms according to an illustrative embodiment of the invention, while FIG. 2B depicts a side view of the intracardiac occluder illustrated in FIG. 2A. As shown, the intracardiac occluder 50 includes, for example, a proximal occlusion shell 52 (i.e., an occlusion shell that is closest to an operator of the intracardiac occluder 50 (e.g., a physician)) and a distal occlusion shell 54. While the occlusion shells depicted in FIGS. 2A-B are rectangular, the shell may be circular, elliptical, square, concave, convex, flat or any other functional shape.

In one embodiment, the proximal occlusion shell 52 includes a proximal support frame 56, and the distal occlusion shell 54 includes a distal support frame 58. In one embodiment, the proximal support frame 56 and the distal support frame 58 are part of an overall support structure 60 that also includes a central body portion 27. The central body portion 27, for example, joins the proximal occlusion shell 52 to the distal occlusion shell 54. For example, in one embodiment, the proximal support frame 56 of the proximal occlusion shell 52 is joined by the central body portion 27 to the distal support frame 58 of the distal occlusion shell 54. In another embodiment, the central body portion 27 joins the center of the proximal occlusion shell 52 to, for example, the center of the distal occlusion shell 54.

With continued reference to FIGS. 2A-B, according to the invention, in one embodiment, the distal occlusion shell 54 includes a scaffold material 53 supported by the distal support frame 58. In another embodiment, the proximal occlusion shell 52 includes a scaffold material 51 supported by the proximal support frame 56. In one embodiment, the scaffold material 51, 53 of the proximal occlusion shell 52 and the distal occlusion shell 54 are made from a biological tissue scaffold, such as collagen. For example, the scaffold material 51, 53 may be comprised of collagen and other native components derived from, for example, the tunica submucosa layer of the porcine small intestine, or other sources as described in, for example, U.S. patent application Publication Ser. No. 2004-0098042, incorporated by reference herein. Alternatively, the scaffold material 51, 53 may be made from a synthetic material, such as a polyester fabric, expanded polytetrafluoroethylene (ePTFE), a polyvinyl alcohol sponge, such as Ivalon®, or a metal mesh, for example.

Referring still to FIGS. 2A and 2B, in one embodiment according to the invention, the support frames 56, 58 comprise a plurality of arms, generally, 20, for example, four arms 20, 20', 20'', 20'''. Each arm 20 extends from a hub 22. In one embodiment, the hub 22 is connected to the central body portion 27. In one embodiment, the intracardiac occluder of the invention includes an occlusion shell 52, 54 with no arms. In another embodiment, the support frame 56, 58 of the occlusion shell 52, 54 has one, two, three, four, five, six, seven, eight, nine, ten, or more arms.

With continued reference to FIGS. 2A-2B, in one embodiment, at least one arm 20 is curved, while in another embodiment, at least one arm 20 is straight. Furthermore, in one embodiment, the intracardiac occluder of the invention includes only one occlusion shell, for example, a proximal occlusion shell 52 or a distal occlusion shell 54. In another embodiment, the intracardiac occluder includes two occlusion shells 52, 54, for example, a proximal occlusion shell 52 and a distal occlusion shell 54. In one embodiment having two occlusion shells 52, 54, the proximal occlusion shell 52 has the same number of arms 20 as the distal occlusion shell 54, while in another embodiment, the proximal occlusion shell 52 has a different number of arms 20 than the distal occlusion shell 54.

Furthermore, with continued reference to FIG. 2A, while the arms 20 are depicted each as one continuous length extending from the hub 22 to the free end 24, in another embodiment of the invention, an arm 20 may be disrupted in its length by a joint (not shown) to impart additional flexibility along the length of the arm 20. As used herein, a joint is defined as an articulating joint, i.e., requiring the juncture of two parts. In a particular embodiment, one or more arms 20 are joint-free, i.e., do not have an articulating joint. In a particular embodiment, a joint-free arm 20 is modified to impart additional flexibility by incorporating one or more coils, springs (not shown) or any other non-articulating modification or combination that would improve flexibility at a specific point anywhere along the length of an arm 20, for example as described in U.S. patent application entitled "Multi-Strand Septal Occluder," co-filed with this application on Mar. 16, 2006, having Ser. No. 11/377,010.

Figure 3A:
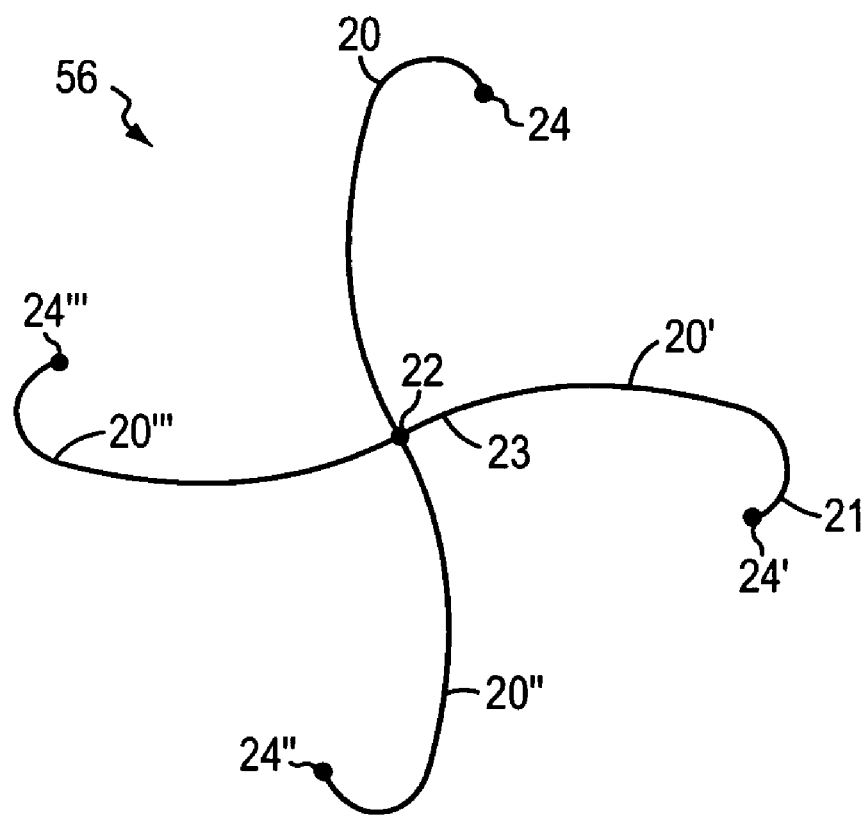
FIG. 3A depicts a top plan view of an exemplary support frame of an occlusion shell of an intracardiac occluder, according to an illustrative embodiment of the invention.
Figure 3B:
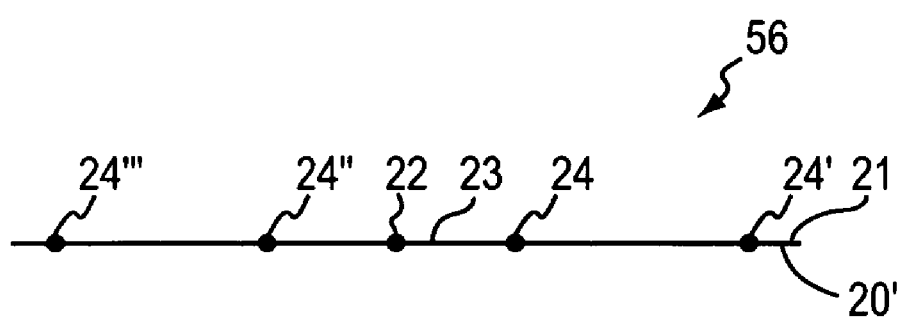
FIG. 3B depicts a side view of the exemplary support frame of an occlusion shell of an intracardiac occluder, illustrated in FIG. 3A, according to an illustrative embodiment of the invention.

FIG. 3A depicts a top plan view of an exemplary support frame of an occlusion shell of an intracardiac occluder, while FIG. 3B depicts a side view of the exemplary support frame shown in FIG. 3A, according to an illustrative embodiment of the invention. The support frame 56, 58 may be used as a proximal support frame 56 or as a distal support frame 58. The support frame 56, 58 has four curved arms 20, 20', 20'', 20'''.

As depicted in FIG. 3A, each arm 20 is curved. In one embodiment, the curve of the arm 20 extends from the hub end 23 to the free end 21. For example, according to one embodiment of the invention, an arm 20 is continuously curved over its entire length such that no part of the arm 20 is straight.

In a further embodiment, each arm of the support frame 56, 58 curves such that the hub end 23 and the free end 21 of each arm 20 remain in the same plane as all points on that arm 20. In a particular embodiment, each arm 20 of the support frame 56, 58 curves such that the hub end 23 and the free end 21 of each arm 20 remain in the same plane as the hub end 23 and free end 21 of each other arm 20. In a further embodiment, each arm 20 of the support frame 56, 58 curves such that the hub end 23 and the free end 21 of each arm 20 remain in the same plane as the hub end 23, free end 21 and each other point on each other arm 20, resulting in a two-dimensional or planar profile of the support frame 56, 58 as exemplified in FIG. 3B.

In another embodiment, while each arm 20 of the support frame 56, 58 of the occlusion shell 52, 54 curves such that the hub end 23 and the free end 21 of each arm 20 remain in the same plane as all points on that arm 20, at least a second arm 20, including its hub end 23, free end 21, and all points on the second arm 20 are in a different plane than the hub end 23, free end 21, and all other points on at least one other arm 20 (not shown). The result is a three-dimensional or non-planar support frame 56, 58.

For example, in one embodiment, the plane of one arm 20, including the hub end 23, free end 21 and all points on the arm 20, intersects the plane of at least a second arm 20, where the plane of the second arm 20 includes the hub end 23, free end 21, and all points on the second arm 20. In another embodiment, the plane of one arm 20 including the hub end 23, free end 21, and all points on that arm 20 intersects at an angle of 90 degrees the plane of at least a second arm 20, where the plane of the second arm 20 includes the hub end 23, free end 21, and all points on the second arm 20. In another embodiment, the angle of intersection is less than 90 degrees. In a further embodiment, the plane of at least one arm 20 including the hub end 23, free end 21 and all points on the arm 20, does not intersect the plane of at least a second arm 20 including the hub end 23, free end 21 and all points on the second arm 20.

With continued reference to FIGS. 3A-B, each of the arms 20 of the support frame 56, 58 curves, for example, in the same direction. As shown in FIG. 3A, the curvature of each arm 20 is in a clockwise direction, for example, when following the direction of the curve from the hub end 23 to the free end 21. Alternatively, one or more arms 20 may curve in a counter-clockwise direction when following the direction of the curve from the hub end 23 to the free end 21. In yet another embodiment, at least one arm 20 curves in a clockwise direction while at least one arm 20 curves in a counter-clockwise direction. In one embodiment, at least a first arm 20 curves in a direction opposite to that of a second arm 20. In one embodiment, as shown in FIG. 3A, an atraumatic tip 24 is fixed on the free end 21 of each arm 20.

Figure 4A:
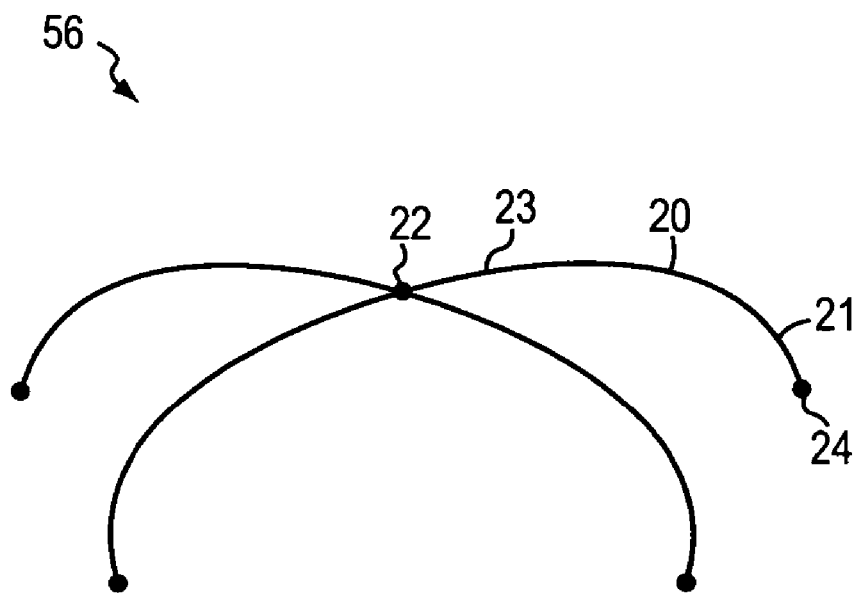
Figure 4B:
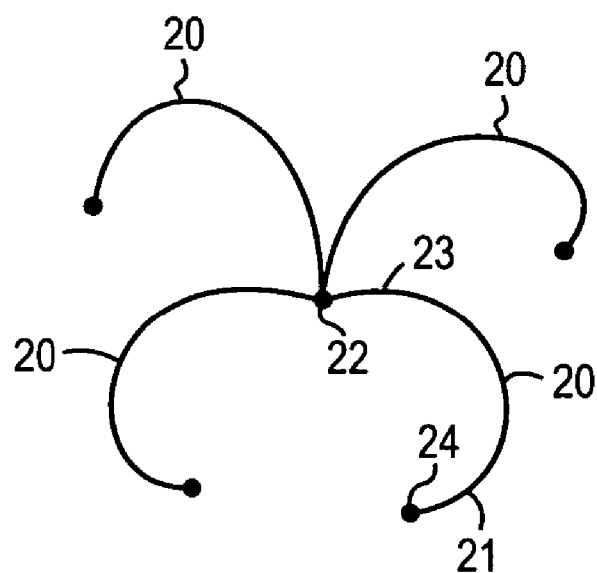
FIG. 4B depicts a top plan view of the support frame depicted in FIG. 4A, according to an illustrative embodiment of the invention.

FIG. 4A depicts a side view of an exemplary support frame of an occlusion shell of an intracardiac occluder including helically curved arms, while FIG. 4B depicts a top plan view of the support frame depicted in FIG. 4A, according to an illustrative embodiment of the invention. In one embodiment, a helically curved arm 20 has a curve extending from the hub end 23 to the free end 21 having less than one full turn, i.e., less than 360°, whereas, in another embodiment, (not shown), a helically curved arm 20 includes a curve extending from the hub end 23 to the free end 21 having a full turn, i.e., 360°. In a further embodiment, a helically curved arm 20 includes a curve extending from the hub end 23 to the free end 21 including more than one full turn, i.e., greater than 360°.

As used herein, a helically curved arm 20, in one embodiment, comprises a spiral. In a further embodiment, a helically curved arm 20 includes a continuous curve or portion thereof traced by a point moving around fixed point in the same plane while steadily increasing or diminishing its distance from the fixed point, like a watch-spring. In one embodiment, the helically curved arm 20 including the curve traced by a point moving around the fixed point in the same plane includes less than one full turn, whereas in another embodiment, the curve includes more than one full turn, i.e., a turn of greater than 360°. In a further embodiment, the helically curved arm 20 includes a curve including at least one full turn and at least one less than full turn. In yet another embodiment, the curve of the helically curved arm 20 extends from the hub end 23 of the arm 20 to the free end 21 of the arm 20.

In another embodiment, a helically curved arm 20 is a corkscrew or a coil. In a further embodiment, the helically curved arm 20 comprises a curve or portion of a curve traced by a point moving around and simultaneously advancing along a cylinder or cone. In one embodiment, the curve advances along a cylinder such the diameter of each turn in the curve is constant. In another embodiment, the curve advances around a cone such that the diameter of each consecutive turn of the curve increases, whereas in another embodiment, the curve advances around a cone such that the diameter of each consecutive turn of the curve decreases.

In yet another embodiment, a helically curved arm 20 comprises a curve or a portion of a curve extending from a hub end 23 to a free end 21 in a constantly changing plane around a central axis. In another embodiment, a helically curved arm 20 includes a curve formed by a straight line traced on a plane when the plane is wrapped around a cylinder, i.e., a curve that when unrolled into a plane becomes a straight line. In one embodiment, the distance between a first turn and a second turn of the helically curved arm 20 and the second turn and a third turn of the helically curved arm 20 is constant, while in another embodiment, the distance between the first turn and the second turn, and the second turn and the third turn is different.

With reference to FIG. 4A, in one embodiment, each helically curved arm 20 of the support frame 56, 58 of the occlusion shell 52, 54 curves in the same direction. For example, in one embodiment each helically curved arm 20 curves clockwise while in another embodiment, each helically curved arm 20 curves in a counter-clockwise direction, the direction of the curve being determined by following curve from the hub end 23 to the free end 21. As shown in FIG. 4B, according to one embodiment, at least one helically curved arm 20 curves in a different direction than a second helically curved arm 20. For example, one helically curved arm 20 curves in a clockwise direction, while a second helically curved arm 20 curves in a counter-clockwise direction. A helically curved arm 20 curving in one direction may be adjacent to at least one arm 20 curving in another direction, or it may be adjacent to at least one arm 20 curving in the same direction. Furthermore, in one embodiment of the invention, the support frame 56, 58 of the occlusion shell 52, 54 includes at least one helically curved arm 20 along with an arm 20 that curves such that the free end 21 and the hub end 23 remain in the same plane as all other points on the arm 20, such as, for example, an arm 20 of the configuration shown in FIG. 3A.

Figure 5A:
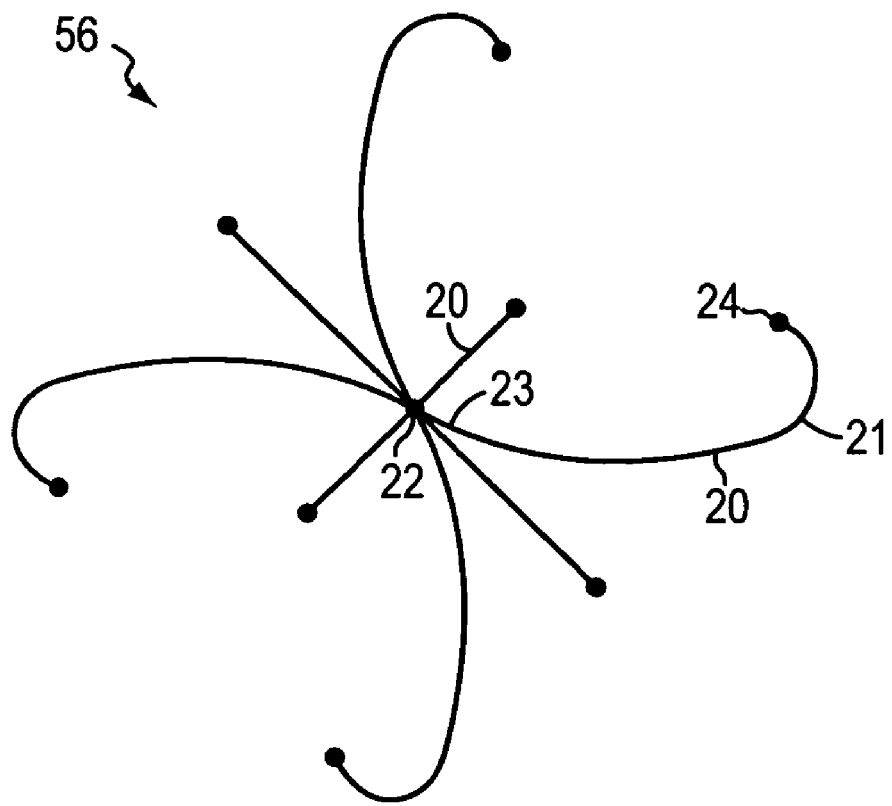
FIG. 5A depicts a top plan view of an exemplary support frame of an occlusion shell of an intracardiac occluder, according to another illustrative embodiment of the invention.
Figure 5B:
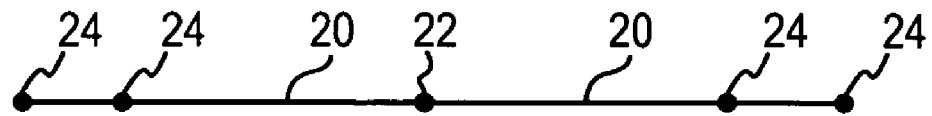
FIG. 5B depicts a side view of the exemplary support frame for an occlusion shell of an intracardiac occluder illustrated in FIG. 5A, according to an illustrative embodiment of the invention.

FIG. 5A depicts a top plan view of an exemplary support frame of an occlusion shell of an intracardiac occluder, wherein at least one arm 20 is curved and at least one arm 20 is straight, according to an illustrative embodiment of the invention. FIG. 5B depicts a side view of the support frame of FIG. 5A, according to an illustrative embodiment of the invention.

The support frame 56, 58 shown can be used either as the proximal occlusion shell support frame 56 or the distal occlusion shell support frame 58. As shown in FIG. 5B, the arms 20 curve such that the free end 21 and the hub end 23 of the arm 20 remain in the same plane as all other points on the arm 20. In yet another embodiment, the arms 20 curve continuously from the hub end 23 to the free end 21. In one embodiment of the invention, a proximal support frame 56 or distal support frame 58 may have at least one straight arm 20 as shown in FIGS. 5A-B, and at least one arm 20 that curves helically, for example, such as an arm shown in FIG. 4. Alternatively, in another embodiment, at least one arm 20 includes a curve with the free end 21 of the arm 20 being in the same plane as the hub end 21 of the arm 20 and all other points on the arm 20, as shown in FIG. 3A. Furthermore, in yet another embodiment, the support frame 56, 58 may have one or more arms 20 that are shorter in length than one or more of the other arms 20. For example, as shown in FIG. 5A, in one embodiment, a first straight arm 20 is longer than a second straight arm 20, while in another embodiment, (not shown), a first curved arm 20 is longer than a second curved arm 20.

Figure 6A:
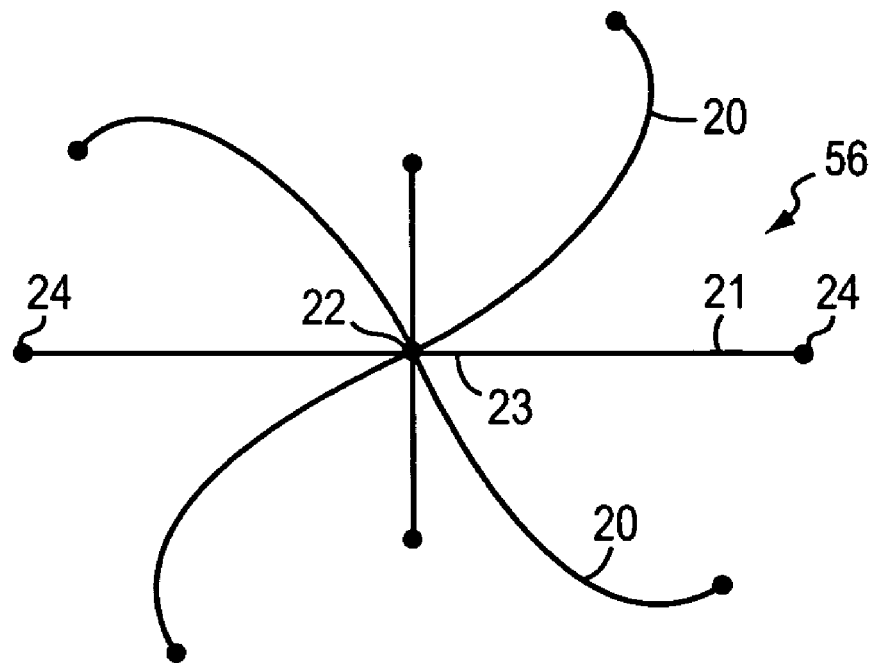
FIG. 6A depicts a top plan view of yet another exemplary support frame of an occlusion shell of an intracardiac occluder, according to an illustrative embodiment of the invention.
Figure 6B:
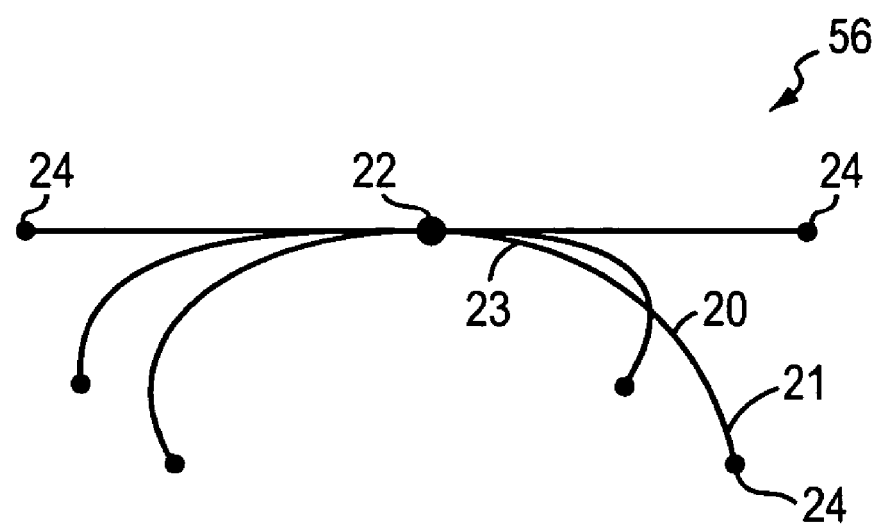
FIG. 6B depicts a side view of the exemplary support frame of an occlusion shell of an intracardiac occluder as depicted in FIG. 6A, according to an illustrative embodiment of the invention.

FIG. 6A depicts a top plan view of yet another exemplary support frame of an occlusion shell of an intracardiac occluder, according to an illustrative embodiment of the invention. In the illustrative embodiment, a first arm 20 is curved and a second arm 20 is straight. FIG. 6B depicts a side view of the exemplary support frame of an occlusion shell of an intracardiac occluder as depicted in FIG. 6A, according to an illustrative embodiment of the invention. In one embodiment, the arms 20 curve helically, while in another embodiment, the arms 20 curve continuously from a hub end 23 to a free end 21. In one embodiment, according to the invention a first arm 20 is a different length than a second arm 20. For example, a variety of lengths of both curved and straight arms 20 may form the support frame 56, 58 for an intracardiac occluder 50. Varying the length of one or more arms 20, either straight arms 20 or curved arms 20, of the support frame 56, 58 of an intracardiac occluder 50 improves the sealing of the device at the location of the intracardiac defect, for example, against the septum of the heart. By using a variety of lengths and types of curved arms 20 (i.e. helical curve, planar curve) in a variety of combinations with other curved and/or straight arms 20 gives the intracardiac occluder 50 enhanced flexibility. Enhanced flexibility aids the occluder 50 in conforming to the irregular anatomy of the intracardiac defect 14. This results in improved sealing and apposition of the device to the tissue, for example, the septum of the heart, reduces the possibility of perforation of cardiac tissues and erosion of the occluder, and reduces fractures of the occluder due to cyclic fatigue, thereby leading to increased intracardiac defect closure rates and improved defect closure.

Figure 7A:
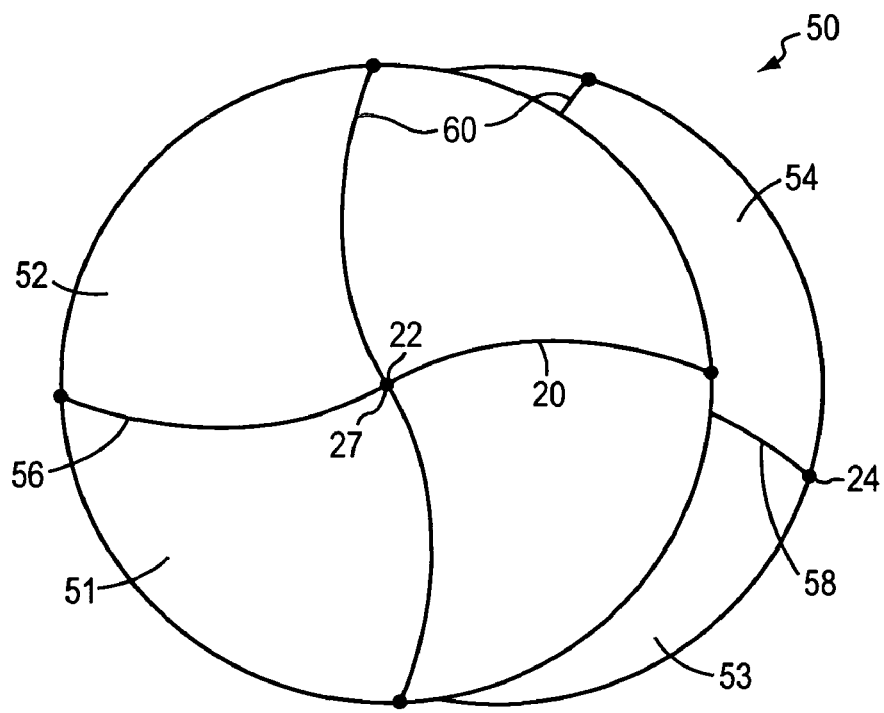
FIG. 7A depicts the proximal and distal occlusion shells of an exemplary curved arm intracardiac occluder, according to an illustrative embodiment of the invention.
Figure 7B:
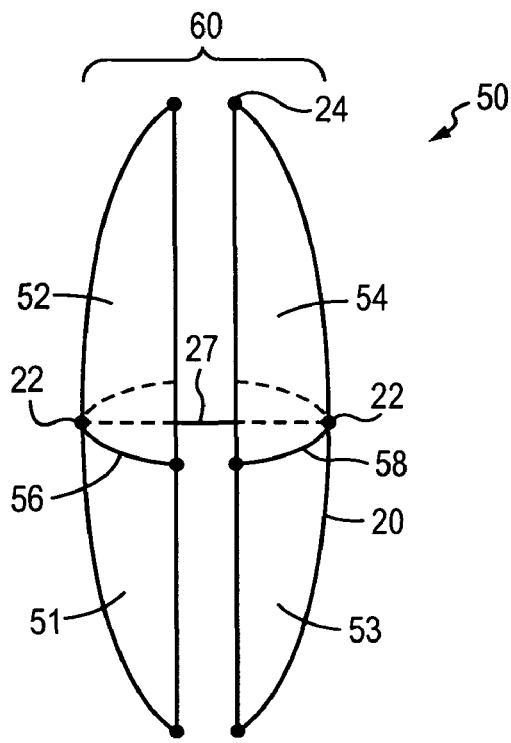
FIG. 7B depicts a side view of the intracardiac occluder illustrated in FIG. 7A, according to an illustrative embodiment of the invention.

FIG. 7A depicts the proximal and distal occlusion shells of an exemplary curved arm intracardiac occluder, according to an illustrative embodiment of the invention. FIG. 7B depicts a side view of the intracardiac occluder of FIG. 7A, according to an illustrative embodiment of the invention. In one embodiment, the occlusion shells 52, 54 are circular in shape. As shown in FIG. 7B, curved arms 20 of the support frames 56, 58 of the proximal and distal occlusion shells 52, 54 may be used to make concave occlusion shells. Referring again to FIG. 2B, when the occlusion shell 52, 54 is rectangular, it is also possible for the occlusion shell 52, 54 to be concave. Any geometric shape can be used for the concave occlusion shell 52, 54, such as a circle, an oval, a square, or any other geometric shape. Regardless of the shape of the occlusion shells 52, 54, the diameter or width of the intracardiac occluder 50 should range from 12 mm to 50 mm. For example, the width of an occlusion shell in one embodiment is optimally between 12 mm and 50 mm. A concave occlusion shell can result in improved sealing and sealing apposition of the device to the tissues of the intracardiac defect resulting in improved defect closure rates and improved defect closure.

Figure 8:
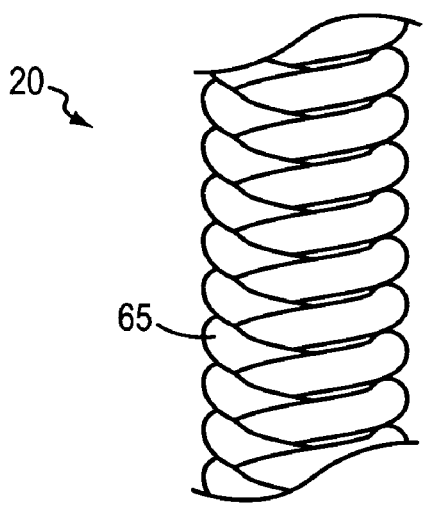
FIG. 8 and FIG. 9 each depict a portion of an arm of an intracardiac occluder wherein the arm is made of a braided or woven material according to illustrative embodiments of the invention.
Figure 9:
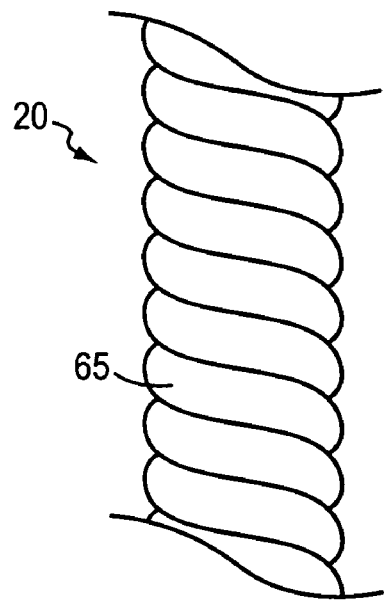

FIG. 8 and FIG. 9 each depict a portion of an arm 20 of an intracardiac occluder 50, according to the invention described herein, made of braided strands 65 or woven strands 65, according to an illustrative embodiment of the invention. The braided or woven material may be any suitable metal or alloy material such as nitinol, MP35N, stainless steel, or any suitable polymer or bioresorbable polymer. The braided or woven material imparts greater flexibility to an arm 20, allowing for improved conformability of the device to the intracardiac defect 14. FIG. 8 depicts one embodiment of an arm 20, for example, made of a braided or woven material, while FIG. 9 depicts another embodiment. According to one embodiment of the invention, an arm 20 may be made of any braided, woven, plaited, twisted, bundled or coiled material suitable to impart increased flexibility to the arm 20.

Figure 10:
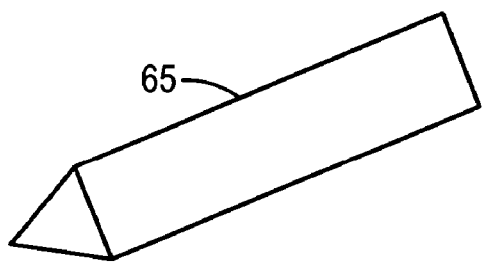
FIGS. 10-12 each depict the three-dimensional geometry of a portion of a strand making up the braided or woven material as shown in FIGS. 8-9, according to an illustrative embodiment of the invention.
Figure 11:
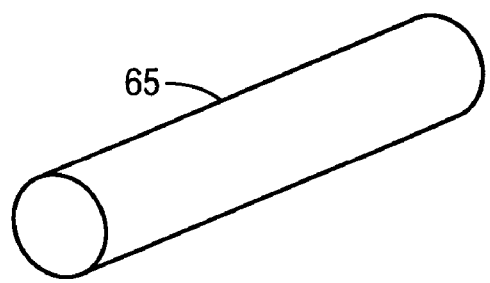
Figure 12:
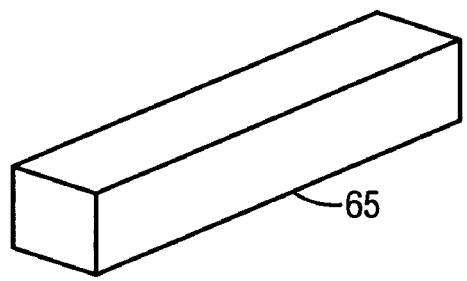

FIGS. 10-12 each depict the three-dimensional geometry of the individual strands 65 making up the braided or woven material made from the strands as shown in FIGS. 8-9, according to an illustrative embodiment of the invention. As FIGS. 10-12 show, the exemplary braided or woven material may be constructed from individual strands 65 with various cross-sectional geometries including, but not limited to a square, a circle, or a triangle. For example, a strand 65 may have any polygonal or oval shaped cross-section possible, such as a rectangular, a rhomboidal, a trapezoidal, an octagonal, a pentagonal, and a hexagonal cross-section. A braided, bundled or woven material may comprise at least two or more strands 65. Using braided or woven material comprised of strands 65 of varying geometrical cross-sections can reduce point pressure exerted by the arms 20 of the intracardiac occluder 50, thus reducing trauma to tissues surrounding the intracardiac defect and enhancing defect closure. In another embodiment, a solid material, rather than a braided or woven material is used to construct the arms 20 of the occlusion shell support frame 56, 58.

Figure 13A:
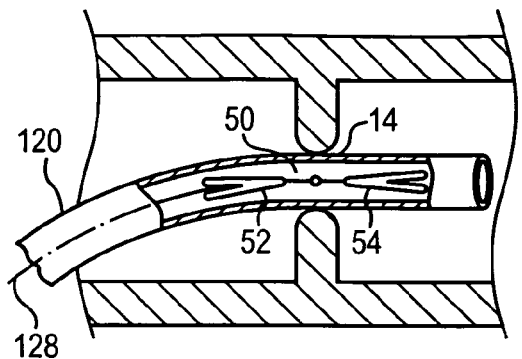
FIGS. 13A-E depict exemplary multiple steps used to insert an intracardiac occluder according to the invention in a defect in a patient's heart.

FIGS. 13A-13E depict exemplary multiple steps used to insert an intracardiac occluder according to the invention in a defect in a patient's heart. The intracardiac occluder 50 according to the invention described above is delivered percutaneously and transvascularly via a catheter 120 including a positioning wire 128 and guided to a predetermined location, for example, a PFO 14. Specifically, as shown in FIG. 13A, a collapsed intracardiac occluder 50 is inserted into a catheter 120 with the distal occlusion shell 54 collapsed and positioned distally to the collapsed proximal occlusion shell 52. The catheter 120, with the collapsed occluder 50 contained in a distal portion thereof is inserted into a blood vessel of a patient and is navigated through the patient's blood vessels into the heart and across the intracardiac defect 14, for example, a PFO.

Figure 13B:
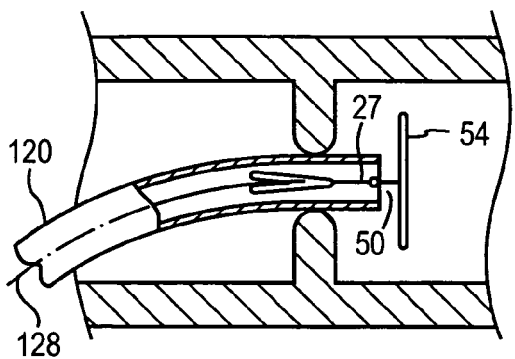

Once the catheter is appropriately positioned in the patient's heart, as shown in FIG. 13B, the intracardiac occluder 50 is moved distally relative to the catheter 120 to cause the distal occlusion shell 54 to exit the distal end of the catheter 120. Such relative movement can be accomplished either by advancing the intracardiac occluder 50 by means of, for example, a positioning wire 128 while holding the catheter in place, or by retracting the catheter 120 while holding the intracardiac occluder in place with the positioning wire 128. Once the distal occlusion shell 54 has advanced beyond the distal end of the catheter 120, the occlusion shell 54 will automatically and resiliently open to its expanded configuration.

Figure 13C:
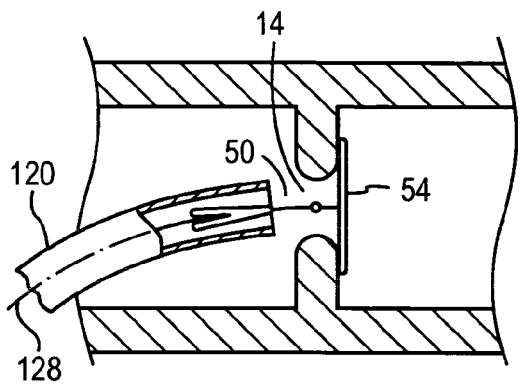
Figure 13D:
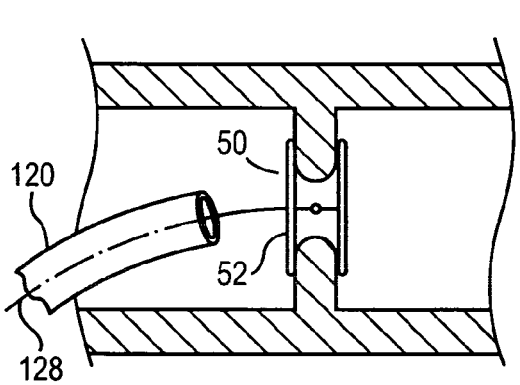
Figure 13E:
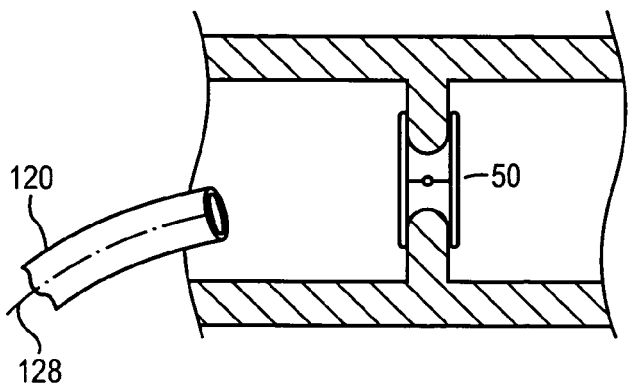

As shown in FIG. 13C, the catheter 120 and intracardiac occluder 50 are then gently retracted to seat the distal occlusion shell 54 against the distal wall of the PFO 14 to occlude the defect 14. As shown in FIG. 13D, the catheter 120 is further withdrawn proximally to allow the proximal occlusion shell 52 to be released from the distal end of the catheter 120. Once released, the proximal occlusion shell 52 opens automatically and resiliently in the same manner as the distal occlusion shell 54. Upon opening, the proximal occlusion shell 52 lies against the proximal wall of the intracardiac defect 14 thereby occluding the defect 14 on the proximal side.

Once the deployment of the occluder 50 is complete, the catheter 120 and position wire 128 are then withdrawn from the patient leaving the opened intracardiac occluder 50 with the occlusion shells 52, 54 positioned on each side of the intracardiac defect 14, for example, a PFO. Because the occlusion shells 52, 54 are free to move relative to each other about the central body portion 27, the intracardiac occluder 50 can be used in applications in which it is desirable that the occluder elements are not directly opposed to one another. For example, such an intracardiac occluder 50 can be used to correct flap-like or tunnel-like defects in the atrial septum.

Variations, modifications, and other implementations of what is described herein will occur to those of ordinary skill in the art without departing from the spirit and the scope of the invention as claimed. Accordingly, the invention is to be defined not by the preceding illustrative description, but instead by the spirit and scope of the following claims.

What is claimed is:

1. An intracardiac occluder, comprising, in its defect occluding state:
   a central body portion extending from a proximal end to a distal end and defining a longitudinal axis, the proximal end coupled to a proximal hub of a proximal occlusion shell and the distal end coupled to a distal hub of a distal occlusion shell, the central body portion being positionable in a defect;
   wherein the proximal occlusion shell comprises a plurality of arms radially extending from the proximal hub, a first arm of the plurality of arms comprising a curve extending from the proximate hub to a first free end in a constantly changing plane around a central axis, and a second arm of the plurality of arms extending in a straight configuration from the proximal hub, perpendicularly of the longitudinal axis, to a second free end.

2. The intracardiac occluder of claim 1, wherein the plurality of arms are joint-free.

3. The intracardiac occluder of claim 1, wherein the first arm and the second arm are adjacent to one another.

4. The intracardiac occluder of claim 1, wherein the plurality of arms are made of a material selected from the group consisting of nitinol, MP35N, polymers, bioresorbable polymers, and a metal.

5. The intracardiac occluder of claim 1, wherein the first arm and the second arm differ in length.

6. The intracardiac occluder of claim 1, wherein the plurality of arms comprises a plurality of wires.

7. The intracardiac occluder of claim 6, wherein the cross-section of at least one of the plurality of wires is a shape selected from the group consisting of a circle, a triangle, a square, a rectangle, and an oval.

8. The intracardiac occluder of claim 1, wherein the proximal shell further comprises a third arm of the plurality of arms comprising a curve extending from the proximal hub to a third free end.

9. The intracardiac occluder of claim 8, wherein the first arm and the third arm curve in the same direction.

10. The intracardiac occluder of claim 8, wherein the third arm extends to the third free end in a constantly changing plane around a central axis.

11. The intracardiac occluder of claim 8, wherein the second arm is adjacent to the third arm.

12. The intracardiac occluder of claim 8, wherein the second arm and the third arm differ in length.

* * * * *